US009289198B2

(12) United States Patent
Ginn et al.

(10) Patent No.: US 9,289,198 B2
(45) Date of Patent: Mar. 22, 2016

(54) LOCATOR AND CLOSURE DEVICE AND METHOD OF USE

(71) Applicant: Cordis Corporation, Fremont, CA (US)

(72) Inventors: Richard S. Ginn, Gilroy, CA (US); Thomas J. Palermo, San Jose, CA (US)

(73) Assignee: CORDIS CORPORATION ( * ) Notice: Subject to any disclaimer, the term of this patent is extended or adjusted under 35 U.S.C. 154(b) by 36 days.

(21) Appl. No.: 14/548,000

(22) Filed: Nov. 19, 2014

(65) Prior Publication Data
US 2015/0080946 A1 Mar. 19, 2015

Related U.S. Application Data

(60) Division of application No. 12/102,728, filed on Apr. 14, 2008, which is a continuation-in-part of application No. 11/244,944, filed on Oct. 5, 2005, now Pat. No. 8,088,144.

(60) Provisional application No. 60/677,859, filed on May 4, 2005, provisional application No. 60/997,461, filed on Oct. 2, 2007.

(51) Int. Cl.
A61B 17/08 (2006.01)
A61B 17/00 (2006.01)

(52) U.S. Cl.
CPC .................. A61B 17/0057 (2013.01)

(58) Field of Classification Search
CPC ................ A61B 17/0057; A61B 2017/00654; A61B 2017/2923
See application file for complete search history.

(56) References Cited

U.S. PATENT DOCUMENTS

| 287,046 A | 10/1883 | Norton |
| 2,969,887 A | 1/1961 | Darmstadt et al. |
| 3,015,403 A | 1/1962 | Fuller |
| 3,678,158 A | 7/1972 | Sussman |
| 3,683,655 A | 8/1972 | White et al. |

(Continued)

FOREIGN PATENT DOCUMENTS

| DE | 3922203 C1 | 10/1990 |
| DE | 19710392 C1 | 7/1999 |

(Continued)

OTHER PUBLICATIONS

E.H. Cassinelli, M.D., et al., "Biochemistry of Intervertebral Disc Degeneration and the Potential for Gene Therapy Applications", SpineLine, The Clinical & News Magazine for Spine Care Professionals, vol. 11, Issue 1, Jan.-Feb. 2001.

(Continued)

Primary Examiner — Elizabeth Houston
Assistant Examiner — Son Dang

(57) ABSTRACT

The present invention is directed to a method for sealing a puncture in a wall of a lumen of a body comprising the steps of deploying a deployment member of a sealing device through an elastic membrane adjacent the wall of the lumen and the puncture, wherein the sealing device includes a sealing element; positioning the sealing element adjacent the wall of the lumen; retracting the deployment member relative to the sealing element to stretch the membrane away from the wall of the lumen; retracting the deployment member relative to the sealing element to allow the elastic nature of the membrane to force the sealing element against the puncture; and retracting the device from the puncture.

9 Claims, 9 Drawing Sheets

(56) References Cited

U.S. PATENT DOCUMENTS

| | | | |
|---|---|---|---|
| 3,757,783 A | 9/1973 | Alley | |
| 3,875,595 A | 4/1975 | Froning | |
| 3,941,127 A | 3/1976 | Froning | |
| 3,944,114 A | 3/1976 | Coppens | |
| 3,952,377 A | 4/1976 | Morell | |
| 3,964,480 A | 6/1976 | Froning | |
| 4,269,174 A | 5/1981 | Adair | |
| 4,301,802 A | 11/1981 | Poler | |
| 4,439,423 A | 3/1984 | Smith | |
| 4,447,915 A | 5/1984 | Weber | |
| 4,509,233 A | 4/1985 | Shaw | |
| 4,525,157 A | 6/1985 | Vaillancourt | |
| 4,586,502 A | 5/1986 | Bedi et al. | |
| 4,638,799 A | 1/1987 | Moore | |
| 4,719,108 A | 1/1988 | Smith | |
| 4,738,658 A | 4/1988 | Magro et al. | |
| 4,741,330 A | 5/1988 | Hayhurst | |
| 4,741,336 A | 5/1988 | Failla et al. | |
| 4,744,364 A | 5/1988 | Kensey | |
| 4,772,287 A | 9/1988 | Ray et al. | |
| 4,802,478 A | 2/1989 | Powell | |
| 4,852,568 A | 8/1989 | Kensey | |
| 4,863,477 A | 9/1989 | Monson | |
| 4,878,893 A | 11/1989 | Chin | |
| 4,878,915 A | 11/1989 | Brantigan | |
| 4,890,612 A | 1/1990 | Kensey | |
| 4,904,260 A | 2/1990 | Ray et al. | |
| 4,968,298 A | 11/1990 | Michelson | |
| 4,998,934 A | 3/1991 | Bernstein | |
| 5,002,557 A | 3/1991 | Hasson | |
| 5,015,247 A | 5/1991 | Michelson | |
| 5,032,125 A | 7/1991 | Durham et al. | |
| 5,061,274 A * | 10/1991 | Kensey | 606/213 |
| 5,108,420 A | 4/1992 | Marks | |
| 5,114,032 A | 5/1992 | Laidlaw | |
| 5,123,926 A | 6/1992 | Pisharodi | |
| 5,190,050 A | 3/1993 | Nitzsche | |
| 5,192,301 A | 3/1993 | Kamiya et al. | |
| 5,232,451 A | 8/1993 | Freitas et al. | |
| 5,258,042 A | 11/1993 | Mehta | |
| 5,290,310 A | 3/1994 | Makower et al. | |
| 5,306,234 A | 4/1994 | Johnson | |
| 5,306,254 A | 4/1994 | Nash et al. | |
| 5,312,435 A | 5/1994 | Nash et al. | |
| 5,318,525 A | 6/1994 | West et al. | |
| 5,334,216 A | 8/1994 | Vidal et al. | |
| 5,334,217 A | 8/1994 | Das | |
| 5,342,393 A | 8/1994 | Stack | |
| 5,383,852 A | 1/1995 | Stevens-Wright | |
| 5,383,905 A | 1/1995 | Golds et al. | |
| 5,411,520 A | 5/1995 | Nash et al. | |
| 5,425,757 A | 6/1995 | Tiefenbrun et al. | |
| 5,443,481 A | 8/1995 | Lee | |
| 5,486,195 A | 1/1996 | Myers et al. | |
| 5,492,763 A | 2/1996 | Barry et al. | |
| 5,522,840 A | 6/1996 | Krajicek | |
| 5,531,759 A | 7/1996 | Kensey et al. | |
| 5,549,633 A | 8/1996 | Evans et al. | |
| 5,549,679 A | 8/1996 | Kuslich | |
| 5,554,162 A | 9/1996 | Delange | |
| 5,562,736 A | 10/1996 | Ray et al. | |
| 5,571,181 A | 11/1996 | Li | |
| 5,571,189 A | 11/1996 | Kuslich | |
| 5,573,994 A | 11/1996 | Kabra et al. | |
| 5,588,424 A | 12/1996 | Insler et al. | |
| 5,588,992 A | 12/1996 | Scott et al. | |
| 5,591,206 A | 1/1997 | Moufarrege | |
| 5,601,556 A | 2/1997 | Pisharodi | |
| 5,674,296 A | 10/1997 | Bryan et al. | |
| 5,676,689 A | 10/1997 | Kensey et al. | |
| 5,681,334 A | 10/1997 | Evans et al. | |
| 5,690,674 A | 11/1997 | Diaz | |
| 5,702,421 A | 12/1997 | Schneidt | |
| 5,707,352 A | 1/1998 | Sekins et al. | |
| 5,713,911 A | 2/1998 | Racenet | |
| 5,720,748 A | 2/1998 | Kuslich et al. | |
| 5,725,554 A | 3/1998 | Simon et al. | |
| 5,728,116 A | 3/1998 | Rosenman | |
| 5,728,122 A | 3/1998 | Leschinsky et al. | |
| 5,728,132 A | 3/1998 | Van Tassel et al. | |
| 5,728,146 A | 3/1998 | Burkett et al. | |
| 5,741,429 A | 4/1998 | Donadio, III et al. | |
| 5,800,549 A | 9/1998 | Bao et al. | |
| 5,800,550 A | 9/1998 | Sertich | |
| 5,814,062 A | 9/1998 | Sepetka et al. | |
| 5,830,125 A | 11/1998 | Scribner et al. | |
| 5,830,171 A | 11/1998 | Wallace | |
| 5,843,124 A | 12/1998 | Hammerslag | |
| 5,853,422 A | 12/1998 | Huebsch et al. | |
| 5,855,601 A | 1/1999 | Bessler et al. | |
| 5,857,999 A | 1/1999 | Quick et al. | |
| 5,861,004 A | 1/1999 | Kensey et al. | |
| 5,865,846 A | 2/1999 | Bryan et al. | |
| 5,871,474 A | 2/1999 | Hermann et al. | |
| 5,871,525 A | 2/1999 | Edwards et al. | |
| 5,879,366 A | 3/1999 | Shaw et al. | |
| 5,888,220 A | 3/1999 | Felt et al. | |
| 5,888,223 A | 3/1999 | Bray, Jr. | |
| 5,888,224 A | 3/1999 | Beckers et al. | |
| 5,893,856 A | 4/1999 | Jacob et al. | |
| 5,893,890 A | 4/1999 | Pisharodi | |
| 5,895,411 A | 4/1999 | Irie | |
| 5,897,593 A | 4/1999 | Kohrs et al. | |
| 5,904,648 A | 5/1999 | Arndt et al. | |
| 5,906,631 A | 5/1999 | Imran | |
| 5,908,428 A | 6/1999 | Scirica et al. | |
| 5,919,200 A | 7/1999 | Stambaugh et al. | |
| 5,941,899 A | 8/1999 | Granger et al. | |
| 5,944,738 A | 8/1999 | Amplatz et al. | |
| 5,954,636 A | 9/1999 | Schwartz et al. | |
| 5,954,766 A | 9/1999 | Zadno-Azizi et al. | |
| 5,964,807 A | 10/1999 | Gan et al. | |
| 5,972,015 A | 10/1999 | Scribner et al. | |
| 5,972,031 A | 10/1999 | Biedermann et al. | |
| 5,984,927 A | 11/1999 | Wenstrom, Jr. et al. | |
| 5,989,230 A | 11/1999 | Frassica | |
| 6,001,130 A | 12/1999 | Bryan et al. | |
| 6,003,517 A | 12/1999 | Sheffield et al. | |
| 6,007,563 A | 12/1999 | Nash et al. | |
| 6,007,570 A | 12/1999 | Sharkey et al. | |
| 6,013,052 A | 1/2000 | Durman et al. | |
| 6,016,806 A | 1/2000 | Webb | |
| 6,020,380 A | 2/2000 | Killian | |
| 6,022,376 A | 2/2000 | Assell et al. | |
| 6,027,525 A | 2/2000 | Suh et al. | |
| 6,030,442 A | 2/2000 | Kabra et al. | |
| 6,033,427 A | 3/2000 | Lee | |
| 6,036,720 A | 3/2000 | Abrams et al. | |
| 6,048,346 A | 4/2000 | Reiley et al. | |
| 6,056,749 A | 5/2000 | Kuslich | |
| 6,066,108 A | 5/2000 | Lundberg | |
| 6,066,154 A | 5/2000 | Reiley et al. | |
| 6,071,292 A | 6/2000 | Makower et al. | |
| 6,077,281 A | 6/2000 | Das | |
| 6,077,291 A | 6/2000 | Das | |
| 6,080,182 A | 6/2000 | Shaw et al. | |
| 6,082,362 A | 7/2000 | Webb | |
| 6,086,608 A | 7/2000 | Ek et al. | |
| 6,093,207 A | 7/2000 | Pisharodi | |
| 6,095,149 A | 8/2000 | Sharkey et al. | |
| 6,099,567 A | 8/2000 | Badylak et al. | |
| 6,122,549 A | 9/2000 | Sharkey et al. | |
| 6,126,675 A | 10/2000 | Shchervinsky et al. | |
| 6,126,682 A | 10/2000 | Sharkey et al. | |
| 6,143,004 A | 11/2000 | Davis et al. | |
| 6,146,380 A | 11/2000 | Racz et al. | |
| 6,146,419 A | 11/2000 | Eaton | |
| 6,156,067 A | 12/2000 | Bryan et al. | |
| 6,174,322 B1 | 1/2001 | Schneidt | |
| 6,174,323 B1 | 1/2001 | Biggs et al. | |
| 6,183,518 B1 | 2/2001 | Ross et al. | |
| 6,197,042 B1 | 3/2001 | Ginn et al. | |
| 6,206,907 B1 | 3/2001 | Marino et al. | |
| 6,206,921 B1 | 3/2001 | Guagliano et al. | |

(56) References Cited

U.S. PATENT DOCUMENTS

| | | |
|---|---|---|
| 6,206,922 B1 | 3/2001 | Zdeblich et al. |
| 6,206,923 B1 | 3/2001 | Boyd et al. |
| 6,221,109 B1 | 4/2001 | Geistlich et al. |
| 6,231,561 B1 | 5/2001 | Frazier et al. |
| 6,240,849 B1 | 6/2001 | Holler |
| 6,248,131 B1 | 6/2001 | Felt et al. |
| 6,258,100 B1 | 7/2001 | Alferness et al. |
| 6,270,515 B1 | 8/2001 | Linden et al. |
| 6,287,290 B1 | 9/2001 | Perkins et al. |
| 6,290,674 B1 | 9/2001 | Roue et al. |
| 6,293,951 B1 | 9/2001 | Alferness et al. |
| 6,296,657 B1 | 10/2001 | Brucker |
| 6,306,114 B1 | 10/2001 | Freeman et al. |
| 6,319,263 B1 | 11/2001 | Levinson |
| 6,327,505 B1 | 12/2001 | Medhkour et al. |
| 6,346,112 B2 | 2/2002 | Adams |
| 6,348,064 B1 | 2/2002 | Kanner |
| 6,379,368 B1 | 4/2002 | Corcoran et al. |
| 6,447,539 B1 | 9/2002 | Nelson et al. |
| 6,458,100 B2 | 10/2002 | Roue et al. |
| 6,464,645 B1 | 10/2002 | Park et al. |
| 6,482,224 B1 | 11/2002 | Michler et al. |
| 6,482,235 B1 | 11/2002 | Lambrecht et al. |
| 6,494,848 B1 | 12/2002 | Sommercorn et al. |
| 6,517,559 B1 | 2/2003 | O'Connell |
| 6,547,810 B1 | 4/2003 | Sharkey et al. |
| 6,554,833 B2 | 4/2003 | Levy et al. |
| 6,626,918 B1 | 9/2003 | Ginn et al. |
| 6,645,225 B1 | 11/2003 | Atkinson |
| 6,656,206 B2 | 12/2003 | Corcoran et al. |
| 6,663,655 B2 | 12/2003 | Ginn et al. |
| 6,682,489 B2 | 1/2004 | Tenerz et al. |
| 6,695,867 B2 | 2/2004 | Ginn et al. |
| 6,699,261 B1 | 3/2004 | Cates et al. |
| 6,702,835 B2 | 3/2004 | Ginn |
| 6,776,784 B2 | 8/2004 | Ginn |
| 6,846,319 B2 | 1/2005 | Ginn et al. |
| 6,860,895 B1 | 3/2005 | Akerfeldt et al. |
| 7,144,411 B2 | 12/2006 | Ginn et al. |
| 7,317,951 B2 | 1/2008 | Schneider et al. |
| 7,361,183 B2 | 4/2008 | Ginn |
| 2001/0003158 A1 | 6/2001 | Kensey et al. |
| 2001/0037808 A1 | 11/2001 | Deem et al. |
| 2001/0052344 A1 | 12/2001 | Doshi |
| 2002/0002386 A1 | 1/2002 | Ginn et al. |
| 2002/0016583 A1 | 2/2002 | Cragg |
| 2002/0022822 A1 | 2/2002 | Cragg et al. |
| 2002/0072767 A1 | 6/2002 | Zhu |
| 2002/0077656 A1 | 6/2002 | Ginn et al. |
| 2002/0077657 A1 | 6/2002 | Ginn et al. |
| 2002/0077658 A1 | 6/2002 | Ginn |
| 2002/0077701 A1 | 6/2002 | Kuslich |
| 2002/0095179 A1 | 7/2002 | Tenerz et al. |
| 2002/0112729 A1 | 8/2002 | DeVore et al. |
| 2002/0183787 A1 | 12/2002 | Wahr et al. |
| 2003/0023267 A1 | 1/2003 | Ginn |
| 2003/0033006 A1 | 2/2003 | Phillips et al. |
| 2003/0045893 A1 | 3/2003 | Ginn |
| 2003/0050665 A1 | 3/2003 | Ginn |
| 2003/0088271 A1 | 5/2003 | Cragg et al. |
| 2003/0139819 A1 | 7/2003 | Beer et al. |
| 2003/0144694 A1 | 7/2003 | Chanduszko et al. |
| 2003/0145865 A1 | 8/2003 | Sterman et al. |
| 2003/0208232 A1 | 11/2003 | Blaeser et al. |
| 2003/0225421 A1 | 12/2003 | Peavey et al. |
| 2004/0059375 A1 | 3/2004 | Ginn et al. |
| 2004/0073242 A1 | 4/2004 | Chanduszko |
| 2004/0098042 A1 | 5/2004 | Devellian et al. |
| 2004/0098121 A1 | 5/2004 | Opolski |
| 2004/0133236 A1 | 7/2004 | Chanduszko |
| 2005/0085854 A1 | 4/2005 | Ginn |
| 2005/0192606 A1 | 9/2005 | Paul et al. |
| 2005/0267528 A1 | 12/2005 | Ginn |

FOREIGN PATENT DOCUMENTS

| | | |
|---|---|---|
| EP | 0432321 B1 | 6/1991 |
| EP | 0700671 A1 | 3/1996 |
| EP | 1033115 A2 | 9/2000 |
| EP | 1078601 A2 | 2/2001 |
| FR | 2639823 | 6/1990 |
| WO | WO 92/05828 | 4/1992 |
| WO | WO 97/26847 | 7/1997 |
| WO | WO 98/02100 | 1/1998 |
| WO | WO 98/19605 A | 5/1998 |
| WO | WO 98/20939 | 5/1998 |
| WO | WO 98/48706 | 11/1998 |
| WO | WO 99/02100 | 1/1999 |
| WO | WO 99/02108 | 1/1999 |
| WO | WO 99/02214 | 1/1999 |
| WO | WO 99/61084 | 12/1999 |
| WO | WO 99/65544 | 12/1999 |
| WO | WO 00/07506 | 2/2000 |
| WO | WO 00/62699 | 10/2000 |
| WO | WO 00/69374 | 11/2000 |
| WO | WO 00/71032 | 11/2000 |
| WO | WO 01/02042 A1 | 1/2001 |
| WO | WO 01/10316 A1 | 2/2001 |
| WO | WO 01/13839 A1 | 3/2001 |
| WO | WO 01/13908 A2 | 3/2001 |
| WO | WO 01/21247 A1 | 3/2001 |
| WO | WO 01/26588 A2 | 4/2001 |
| WO | WO 01/28464 A1 | 4/2001 |
| WO | WO 01/45577 A2 | 6/2001 |
| WO | WO 01/45579 A1 | 6/2001 |
| WO | WO 01/60288 A1 | 8/2001 |
| WO | WO 01/66045 A1 | 9/2001 |
| WO | WO 01/66190 A2 | 9/2001 |
| WO | WO 01/87170 A1 | 11/2001 |

OTHER PUBLICATIONS

K. Nishimura, M.D., et al., "Percutaneous Reinsertion of the Nucleus Pulposus, An Experimental Study", SPINE vol. 23, No. 14, pp. 1531-1539, 1998.

Maurice Hiles, "New Specialty Polymer Products Through Interpenetrating Polymer Network (IPN) Technology—The Development of an Interpenetrating Polymer Network to Contain Mechanically Induced Vibration", Oct. 20-21, 1986, Colony Square Hotel, Atlanta, GA.

Zoltan G. Turi, M.D., "Overview of Vascular Closure", Endovascular Today, Closure Update 2008, pp. 28-37.

* cited by examiner

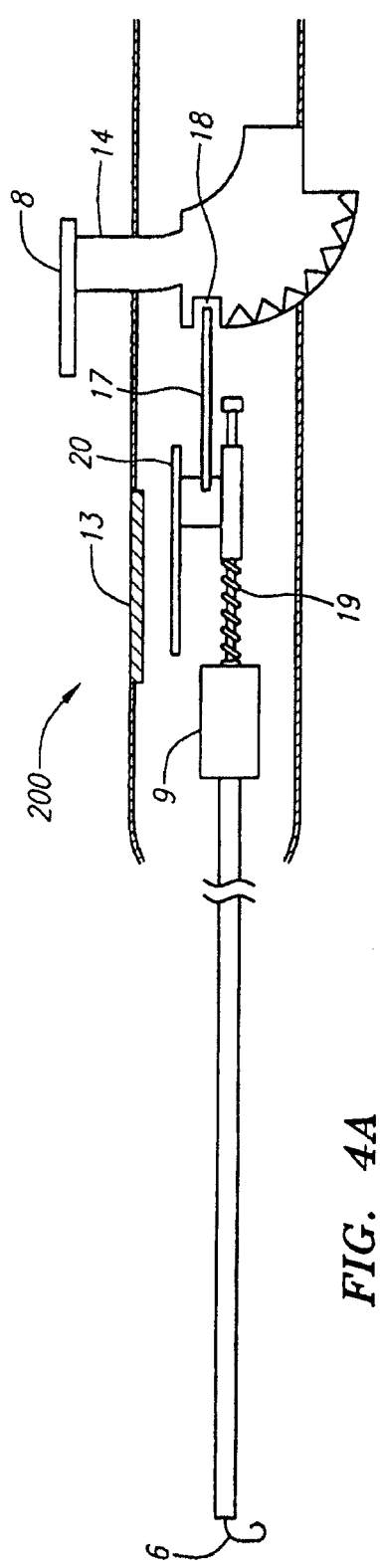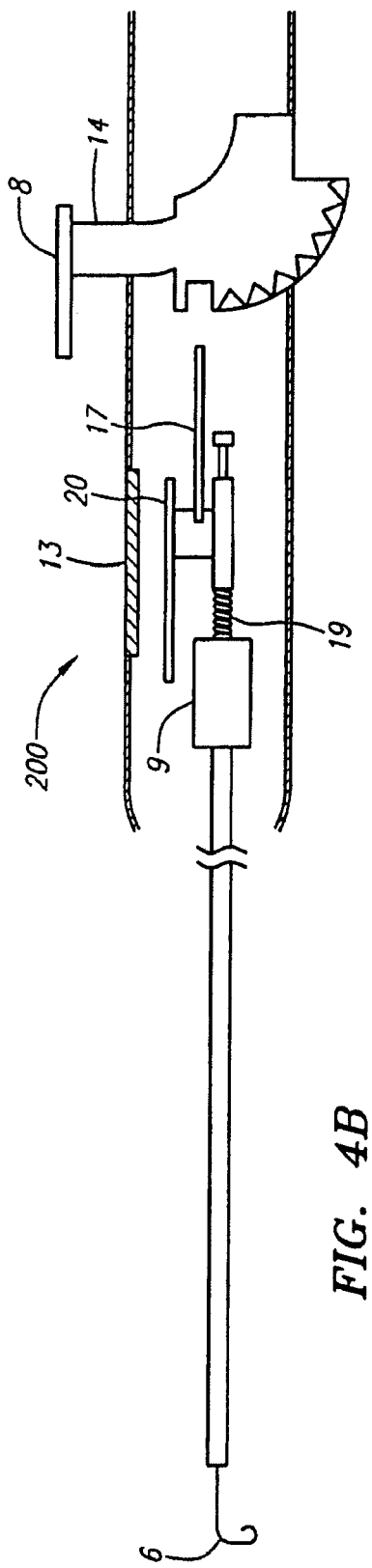
FIG. 4A
FIG. 4B

LOCATOR AND CLOSURE DEVICE AND METHOD OF USE

RELATED APPLICATIONS

This application is a divisional application of U.S. patent application Ser. No. 12/102,728 filed Apr. 14, 2008, which claims the benefit of U.S. Provisional Application Ser. No. 60/997,461 filed on Oct. 7, 2007 and is a continuation-in-part of U.S. patent application Ser. No. 11/244,944 filed on Oct. 5, 2005, which claims the benefit of U.S. Provisional Application Ser. No. 60/677,859, filed May 4, 2005. This application is related to U.S. patent application Ser. No. 10/687,848 filed Oct. 17, 2003 and U.S. patent application Ser. No. 10/850,795, filed May 21, 2004, the disclosures of which are incorporated in their entirety herein.

FIELD OF THE INVENTION

The present invention relates generally to apparatus and methods for sealing or closing passages through tissue, and more particularly to devices for sealing punctures or other openings communicating with body lumens, such as blood vessels, and to apparatus and methods for delivering or deploying such devices.

BACKGROUND OF THE INVENTION

Catheterization and interventional procedures, such as angioplasty and stenting, generally are performed by inserting a hollow needle through a patient's skin and muscle tissue into the vascular system. This creates a puncture wound in a blood vessel, frequently the femoral artery, which, once the interventional procedure has been completed, needs to be closed or sealed in a suitable manner.

Procedures and devices have been proposed for accomplishing such closure which involve the use of an introducer sheath that is placed in the tract of the puncture wound following which a closure delivering device is introduced through the introducer sheath to deploy a sealing element within the tract. An indicator wire may be used to locate the edge of the tract. After the closure delivering device deploys the sealing element, the indicator wire and the device are retracted. Examples of such procedures and devices are disclosed in application Ser. No. 10/687,848, filed Oct. 17, 2003 and Ser. No. 10/850,795 filed May 21, 2004. In these procedures and devices, it would be desirable to exploit features of the patient's anatomy to optimize sealing of the puncture wound.

SUMMARY OF THE INVENTION

A method for sealing a puncture, having an edge, in a wall of a lumen of a body comprising: deploying a deployment member of a sealing device through an elastic tissue membrane adjacent the wall of the lumen and the puncture, wherein the sealing device includes a sealing element; positioning the sealing element adjacent the wall of the lumen; retracting the deployment member relative to the sealing element to stretch the tissue membrane away from the wall of the lumen; retracting the deployment member relative to the sealing element to allow the tissue membrane to engage the sealing element; and retracting the device from the body.

In a preferred embodiment of the invention, the method is performed on a puncture wound in the femoral artery. In the noted embodiment, the elastic tissue membrane is a fascia layer and may comprise a portion of the femoral sheath.

In one aspect of the invention, the sealing element is positioned between the tissue membrane and the wall of the artery lumen when the membrane engages the sealing element. Alternatively, the sealing element partially protrudes from the tissue membrane when the membrane engages the sealing element.

Preferably, the membrane retains the sealing element at a desired position adjacent the wall of the lumen. Also preferably, the tissue membrane urges the sealing element against the wall of the lumen.

In a further embodiment of the invention, the sealing device further includes an indicator wire having a distal tip; and the method further comprises the steps of extending the indicator wire out of the deployment member when the sealing device is deployed through the puncture; adjusting the position of the sealing device until the indicator wire is adjacent to the edge of the lumen puncture; and retracting the indicator wire into the device.

In another aspect of the invention, the method for sealing a puncture comprises the steps of deploying a deployment member of a sealing device through an elastic membrane adjacent the wall of the lumen and the puncture, wherein the sealing device includes a sealing element; positioning the sealing element within the lumen; withdrawing the sealing element outside the lumen adjacent the wall of the lumen; frictionally engaging the membrane with the deployment member; retracting the deployment member relative to the sealing element to stretch the membrane away from the wall of the lumen; disengaging the deployment member from the membrane; and retracting the device from the body.

In a further aspect of the invention, the method for positioning a sealing element within a puncture comprises the steps of deploying a deployment member of a sealing device through an elastic membrane adjacent the wall of the lumen and the puncture; positioning a sealing element carried by the sealing device within the lumen, partially withdrawing the sealing element from the lumen such that the sealing element is disposed partially within the lumen and partially within the puncture when the membrane is elastically displaced; retracting the deployment member to elastically displace the membrane away from the wall of the lumen; deploying the sealing element by releasing it from the sealing device; disengaging the deployment member from the membrane, wherein the membrane elastically holds the sealing member within the puncture and partially within the lumen; and retracting the device from the body.

In yet another aspect of the invention, the method for positioning a sealing element adjacent a puncture comprises the steps of deploying a deployment member of a sealing device through an elastic membrane adjacent the wall of the lumen and the puncture; positioning a sealing element carried by the sealing device adjacent the wall of the lumen, wherein the sealing element is configured to be disposed between the wall of the lumen and the membrane when the membrane is elastically displaced; retracting the deployment member to elastically displace the membrane away from the wall of the lumen; deploying the sealing element by releasing it from the sealing device; disengaging the deployment member from the membrane, wherein the membrane elastically urges the sealing member against the wall of the lumen; and retracting the device from the body.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

DESCRIPTION OF THE DRAWINGS

In order to better appreciate how the above-recited and other advantages and objects of the present inventions are obtained, a more particular description of the invention briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

FIGS. 4(a-b) illustrate a distal portion-of the device in accordance with a preferred embodiment of the present invention.

DETAILED DESCRIPTION OF THE INVENTION

Figure 1:
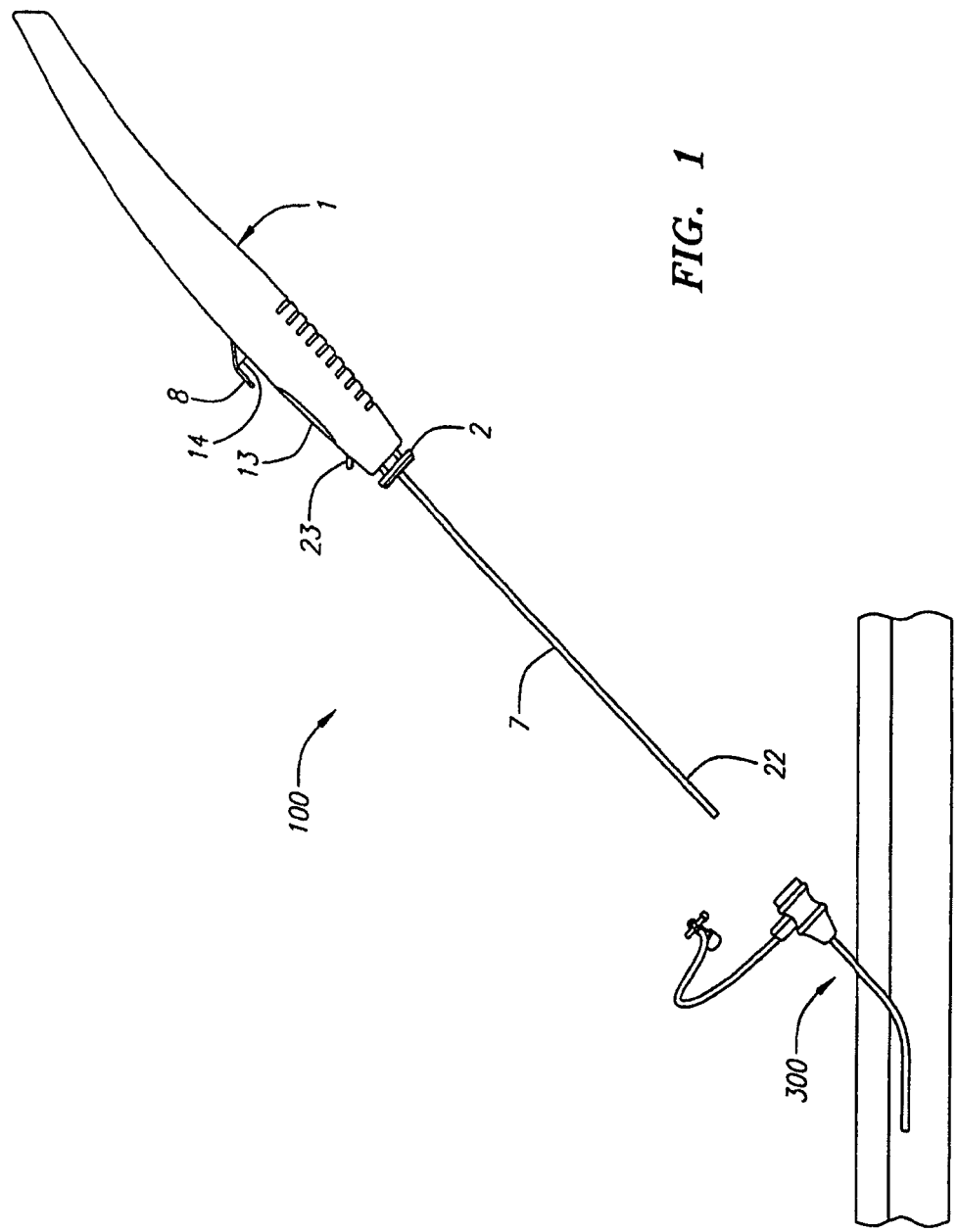
FIG. 1 illustrates a side-view of a sealing element deployment device in accordance with a preferred embodiment of the present invention.

A device 100 for deploying a detachable sealing element 160 (shown in FIG. 2) in a puncture wound is shown in FIG. 1, herein referred to as a closure device 100. Examples of such a sealing element or plug 160 are described in U.S. application Ser. No. 10/687,848, filed Oct. 17, 2003, Ser. No. 10/850,795 filed May 21, 2004, and Ser. No. 11/038,995, filed Jan. 19, 2005, each of which applications are hereby incorporated by reference. Sealing element 160 occludes blood flow from a puncture. In a preferred embodiment, the sealing element 160 will be fabricated from a material which may expand upon contact with blood, such as a felt made from polyglycolic acid and/or polylactic acid polymers or copolymers or other materials such as collagens. The sealing element 160 may also have one or more hemostasis, antibiotic or other therapeutic agents added to it.

Alternatively, in other preferred embodiments, the sealing element 160 will be made in such a manner that it will expand spontaneously or upon removal of a restraining force. In still other embodiments, the sealing element 160 can be expandable mechanically, hydraulically or pneumatically. In all such embodiments, it is preferred that the sealing element 160 be fabricated from a bioabsorbable material.

A presently preferred embodiment employs needle-weaved polyglycolic acid (PGA) fibers that degrade through chemical hydrolysis of unstable bonds in the crystalline phase to lactic acid and glycolic acid, followed by enzymatic attack and participation in the Kreb's cycle to metabolize to carbon dioxide and water. In one embodiment, sealing element 160 exhibits modest expansion in the range of approximately 0-15%.

The closure device 100 for deploying the sealing element 160 includes a tubular elongate member 1, herein referred to as the "housing," which houses various components that will be described below. The device 100 also comprises a wire actuator 2 which is external and distal to the housing 1 and is slidably mounted and configured to actuate an indicator wire 6, as described below. Extending through the distal end of the housing 1 is a deployment tube 7 configured to be received by an introducer sheath 300 known in the art. The deployment tube 7 is slightly longer than the introducer sheath 300. The deployment tube 7 receives an indicator wire 6 (shown in FIGS. 2a and 2b) and a plunger 80, which operates as a backing member supporting a detachable sealing element 160 at a distal section of the deployment tube 7. The plunger 80 preferably includes a channel through which the indicator wire 6 may be received within the tube 7. The channel is preferably located on or near the edge or the periphery of the backing portion of the plunger 80, i.e., near the internal surface of the deployment tube 7. Optionally, an indicator wire tube or other lumen (not shown) may be provided within the interior of the deployment tube 7. The indicator wire tube is preferably attached to the housing 1 at its proximal end, and extends through the deployment tube 7. The indicator wire 6 then extends through the indicator wire tube or other lumen and exits the indicator wire tube at or near the distal end of the deployment tube 7. (Additional details of the structure and operation of the plunger 80 are described in Ser. No. 10/850,795, filed May 21, 2004, which is incorporated by reference.)

The deployment tube 7 includes an inlet port 22 in the distal section of the tube 7, configured to take in blood when exposed to a vessel, and the housing 1 includes an outlet port 23 communicatively coupled to the inlet port 22 for allowing the blood to exit outside of the puncture wound. Also extending out of the housing is a trigger 8 that preferably includes a rotary link 14 configured to deploy the detachable sealing element 160. Before operation of the closure device 100, the rotary link 14 is locked, i.e., the operator is prevented from actuating the rotary link 14 despite pressing the trigger 8, as described below.

Turning to FIGS. 2(A-D), deployment of a detachable sealing element 160 within a puncture wound 400 using the closure device 100 is illustrated. An introducer sheath 300 is already deployed within the tract 410 of the wound 400 with its distal end 310 exposed within the lumen 420 of a blood vessel defined by a vessel wall 430. The deployment tube 7 of the closure device 100 is inserted into the introducer sheath 300. Upon substantially complete insertion, the device 100 is engaged with the introducer sheath 300, and the distal section of the deployment tube 7 extends out of the distal end of the sheath 300. When the inlet port 22 is exposed to the lumen 420 of the vessel 430, blood will enter the inlet port 22 and travel out of the outlet port 23 extending out of the housing 1. The blood exiting the outlet port 23 will be visible to the operator (not shown) of the device 100, notifying the operator that the distal end of the deployment tube 7 is within the lumen 420 of the vessel 430 and outside of the tract 410 of the puncture wound 400.

Also, upon substantially complete insertion, the wire actuator 2 of the device 100 is actuated by the proximal end of the sheath 300, causing the wire actuator 2 to be pushed toward the housing 1. The wire actuator 2 is mechanically coupled to the indicator wire 6 and configured to actuate the indicator wire 6 in the distal direction. Thus, as the wire actuator 2 is pushed towards the housing 1, the wire actuator 2 causes the indicator wire 6 to extend out of the distal end of the deployment tube 7. When the indicator wire 6 exits the tube 7, the distal section of the wire 6 forms into a loop 5 located adjacent the distal tip of the tube 7. The loop 5 of the wire 6 will come into contact with the vessel wall 430 near the edge 415 of the tract 410 when the device 100 and the sheath 300 are withdrawn, as shown in FIG. 2b.

Figure 2A:
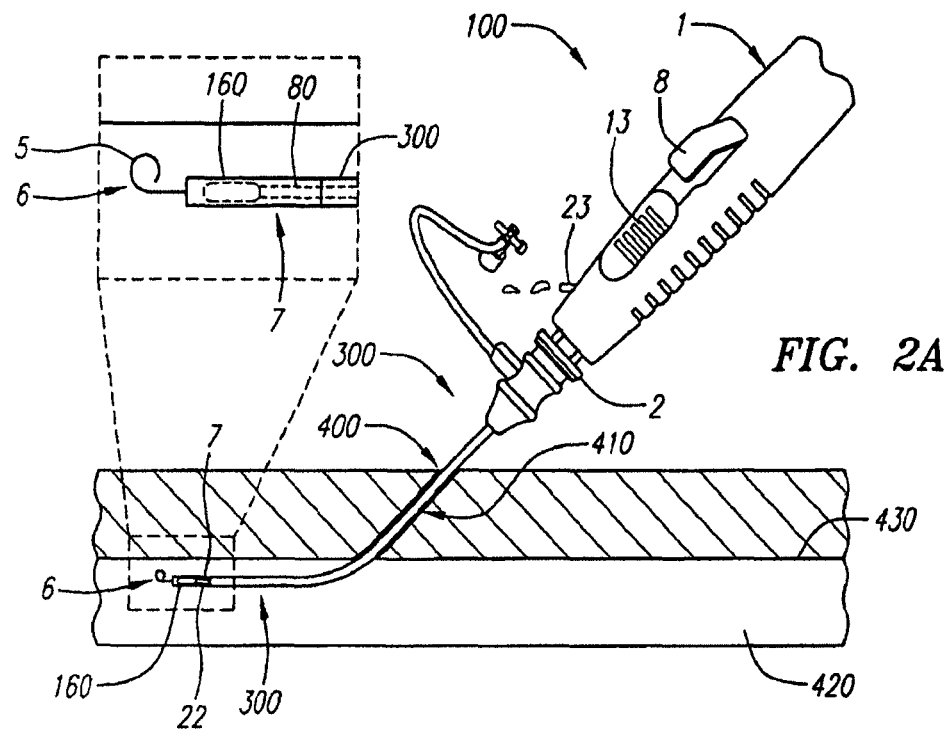
FIG. 2A illustrates a side-view of a sealing element deployment device in accordance with a preferred embodiment of the present invention.
Figure 2B:
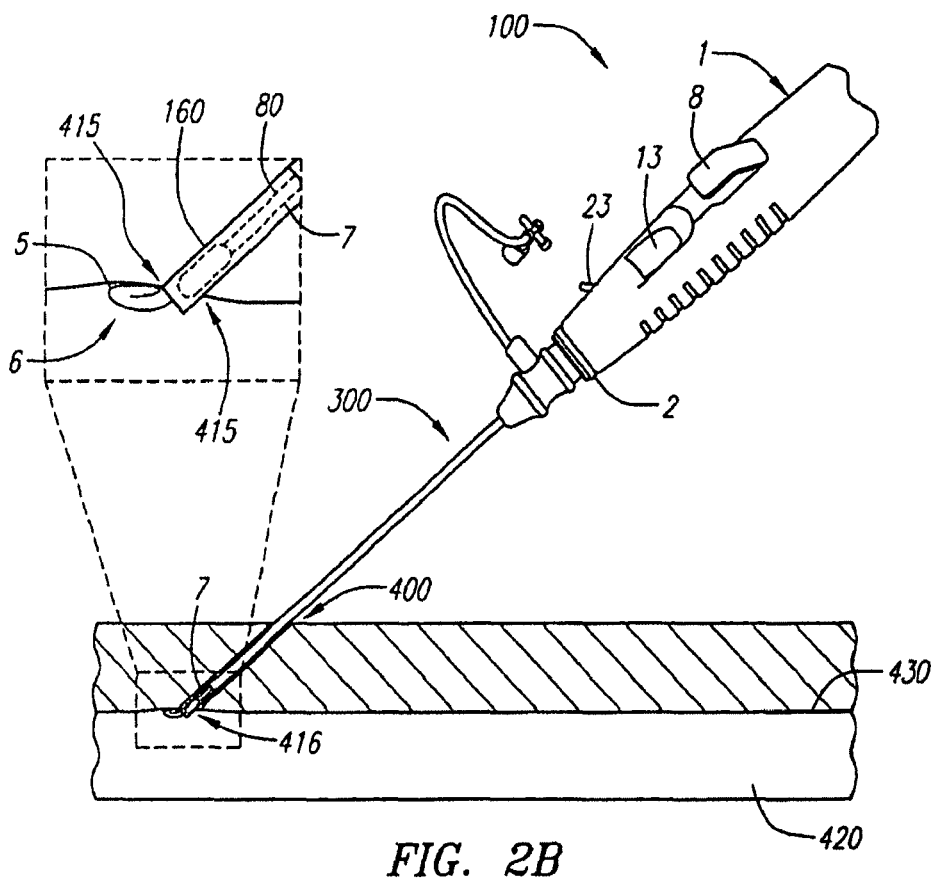
FIG. 2B illustrates a side-view of a sealing element deployment device in accordance with a preferred embodiment of the present invention.

Turning to FIG. 2b, after the device 100 is inserted and engaged into the sheath 300 as described above, the operator withdraws or pulls back the device 100 and sheath 300 within the tract 410. When the distal section of the deployment tube 7 exits the lumen 420 and enters the tract 410, the inlet port 22 is no longer exposed to the blood within the lumen 420 and thus, the blood flow out of the outlet port 23 ceases. This notifies the operator that the distal section of the deployment tube 7 has exited the lumen 420 and entered the tract 410 of the puncture wound 400. The indicator wire's 6 resistance that is caused by the loop 5 engaging the vessel wall 430 will unlock the rotary link 14, as described below, and optionally toggle the indicator window 13 to a state that indicates that the loop 5 has engaged the vessel wall 430 near the edge 415 of the tract 410, which places the distal end of the deployment tube 7 at a desirable location within the tract 410 and substantially adjacent to the edge 415. In the embodiment shown in FIG. 2b, the indicator window 13 toggles from a striped pattern, FIG. 2a, to a solid pattern, as described below.

Figure 2C:
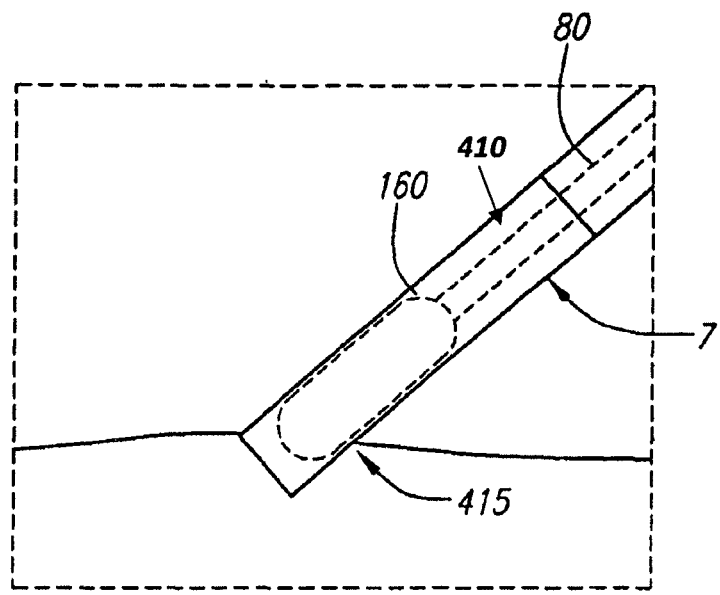
FIG. 2C illustrates a side-view of a distal portion of the sealing element deployment device in accordance with a preferred embodiment of the present invention.
Figure 2D:
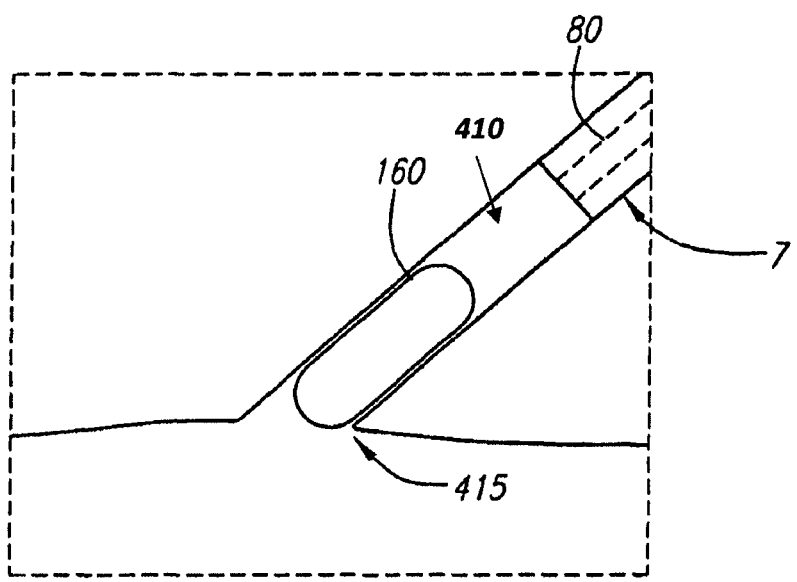
FIG. 2D illustrates a side-view of a distal portion of the sealing element deployment device in accordance with a preferred embodiment of the present invention.

The operator is then enabled to actuate the unlocked rotary link 14 to deploy the sealing element 160 by pressing the trigger 8. Turning to FIGS. 2C and 2D, the rotary link 14 actuates and withdraws both the wire 6 and the tube 7 while the sealing element 160 remains substantially in place by the pusher 80, thereby deploying the sealing element 160. The device 100 then disengages from the sealing element 160, thus sealing or plugging the puncture wound 400. Preferably, in one motion, the rotary link 14 is configured to withdraw the indicator wire 6 into the tube 7 before the tube 7 is withdrawn. Thus, the wire 6 is withdrawn before the sealing element 160 deployed, preventing the wire 6 from interfering with the deployment of the sealing element 160, such as damaging or dislodging the sealing element 160.

Figure 3:
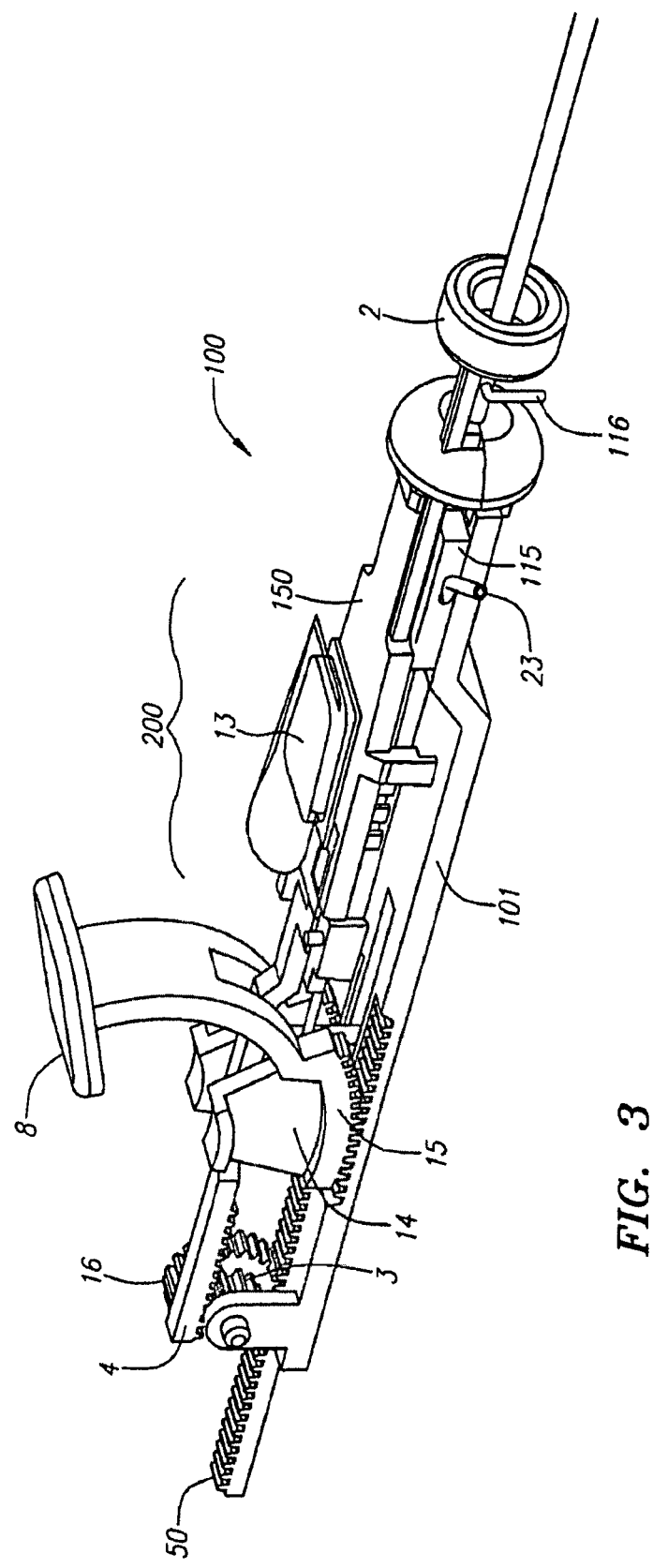
FIG. 3 illustrates a perspective view of components of a sealing element deployment device in accordance with a preferred embodiment of the present invention.

Turning to FIG. 3, a rack and pinion system for actuating the tube 7 and the wire 6 within the housing 1 of the device 100 is shown. The device 100 is shown not engaged to an introducer sheath 300, and thus the wire actuator 2 is in its original state away from the housing 1. The wire actuator 2 is coupled to a first rack 4 that is configured to engage a first gear 3 when the wire actuator 2 is actuated in the proximal direction as described above. The first gear 3 is attached to a second gear 16, which causes a second rack 50 to move in the distal direction. The second rack 50 is engaged with the indicator wire 6, causing the indicator wire 6 to extend out of the tube 7 when wire actuator 2 is actuated by engaging with the introducer sheath 300 as described above. The wire actuator 2 proximally withdraws the first rack 4, which rotates the second gear 16 via the first gear 3, which then advances distally the second rack 50, thus advancing distally the indicator wire 6, causing the indicator wire to extend out of the deployment tube 7.

The first and second gears 3 and 16 share an axis that is secured by a bottom plate 101. The bottom plate 101 is actuated by a trigger that includes a rotary link 14. When the trigger 8 is pressed to deploy the plug 160, the rotary link 14, which includes an arcuate gear section 15 that engages and actuates the bottom plate 101 in the proximal direction, is actuated. A tube collar 115, which is engaged to the deployment tube 7, is anchored at a distal portion of the bottom plate 101. When the bottom plate 101 is withdrawn proximally, the collar tube 115 is withdrawn as well, which in turn withdraws proximally the deployment tube 7, which deploys the plug 160. Proximally withdrawing the bottom plate 101 causes the first gear 3 to rotate along the first rack 4, which is locked in place by the wire actuator 2 engaged with the introducer sheath 300. Proximal to the wire actuator 2 is a post 116 that extends from the housing 1. When the distal portion of the closure device 100 is inserted into the lumen of the introducer sheath 300, a proximal portion of the introducer sheath 300 that defines a lip (not shown) engages the post 116, which connects and locks the closure device 100 to the introducer sheath 300. Thus, the second rack 50 is proximally withdrawn by the second gear 16, which causes the indicator wire 6 to retract substantially simultaneously with the deployment tube 7. The figures show that the first gear 3 has a smaller diameter than the second gear 16. First and second gears 3 and 16 each provide a mechanical advantage to the control of the indicator wire 6 and deployment tube 7 respectively. Preferably, the mechanical advantage regarding the indicator wire 6 is 4:1 and the mechanical advantage regarding the deployment tube 7 is 2:1. Other mechanical advantage relationships may be used e.g., 3:1 for the indicator wire 6 and 1.5:1 for the tube 7. It is preferred that the mechanical advantage for the indicator wire 6 be twice that for the tube 7. Thus, when trigger 8 is depressed, the bottom plate 101 and tube collar 115 will withdraw the tube 7 more slowly than the indicator wire 6 is withdrawn into the device 100 and the indicator wire 6 will be retracted into the deployment tube 7 before the sealing element 160 is deployed and/or disengaged from the tube 7 and the device 100. As described above, this advantageously prevents the indicator wire 6 from interfering with the deployment of the sealing element 160.

One of ordinary skill in the art will appreciate that though a rack and pinion system is described and shown in FIG. 3, any suitable type of actuating system may be configured to retract the indicator wire 6 before a sealing element 160 is deployed and/or disengaged from the device 100 in accordance with a preferred embodiment of the present invention. For example, a hydraulic, electronic, and/or a pulley system may be used instead of or in addition to the rack and pinion system to retract the indicator wire 6 into the deployment tube 7 before the sealing element 160 is deployed and/or disengaged from the device 100.

The housing 1 can also include an indicator assembly 200 coupled to a stationary top plate 150 of the device 100. The indicator assembly 200 can indicate to the operator, via an indicator panel 13 in the top plate 150, whether the distal end of the deployment tube 7 is in the desired location, e.g., near the edge 415 of the tract 410 of the puncture wound. In addition to, or in the alternative, the indicator assembly 200 may further lock the trigger 8 until the deployment tube 7 is in the desired location. In FIGS. 4A and 4B, an implementation of the indicator assembly 200 of the device 100 is shown. The indicator assembly 200 comprises an indicator 20, indicator spring 19 and lockout plate 17. As can be seen from FIG. 4A, a slidable lockout plate 17 engages groove 18 in rotary link 14, thereby preventing substantial movement of rotary link 14. The indicator spring 19 applies a proximal force on the lockout plate 17 to maintain the lockout plate's 17 position even after the indicator wire 6 is deployed from the tube 7.

Turning to FIG. 4B, the indicator wire 6 is fixedly attached to the lockout plate 17, which is coupled to a block 9 via the indicator spring 19. The block 9 is in a secured position, fixed to the housing 1 and/or the tube 7. Because the indicator wire 6 is connected to the tube 7 and/or housing 1 via a spring 19 and slidable lockout plate 17, the indicator wire 6 is capable of axial movement independent of the housing 1 and/or tube 7.

During operation, after the indicator wire 6 has been deployed through the puncture wound 400 with the formed loop 5 exposed to the lumen 420 of a vessel defined by a vessel wall 430, the operator is then ready to withdraw the device 100 and sheath 300 to deploy the sealing element 160 within the tract 410 of the puncture wound 400. Even if blood stops flowing out of the outlet port 23, that only indicates that the inlet port 22 is within the tract 410, not necessarily that the sealing element 160 is desirably near the edge 415 of the tract 410. However, the indicator wire 6 may provide such an indication. When the loop 5 of the wire 6 approaches the edge 415 of the tract 410, the loop 5 will engage the vessel wall 430 near the edge 415 as the device 100 is withdrawn by the operator. When the loop 5 engages the vessel wall 430, it will cause a force to be applied on the wire 6 toward the distal direction, or direction opposite that of the device 100 as its being withdrawn. This force will overcome the force of the spring 19 securing the lockout plate 17, proximally withdraw the lockout plate 17 in the distal direction, and cause the lockout plate 17 to disengage from the groove 18 of the rotary link 14, thereby unlocking the trigger 8. When the trigger 8 is unlocked, because the loop 5 has caught the edge 415, the distal end of the tube 7 is substantially adjacent to the edge 415 of the tract 410, which is a desirable location for the deployment of the sealing element 160. The operator is then enabled to deploy the sealing element 160.

Even though a spring loaded system is described above for locking and unlocking the trigger 8, one of ordinary skill in the art would appreciate that any locking mechanism may be employed in accordance with an embodiment of the present invention, such as a hydraulic and/or electronic system.

In addition to locking and unlocking the trigger 8, the indicator assembly 200 may also provide a visual and/or audio notification to the operator that the distal end of the tube 7 is in a desirable position. As will be explained in more detail with regard to FIGS. 4A, 4B, 5A, 5B, and 6, indicator 20 can be seen through indicator panel 13, which defines two windows 21, on the top plate 150 and indicates to the user when the appropriate time to press trigger 8 with rotary link 14 has been reached.

Figure 5A:
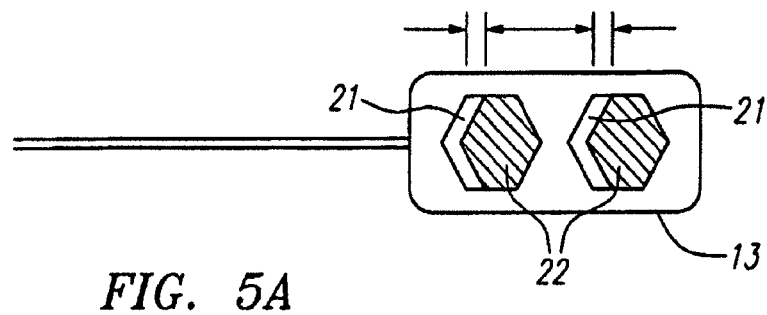
FIGS. 5(a-b) illustrate a top view of a window portion of the sealing element deployment device in accordance with a preferred embodiment of the present invention.
Figure 5B:
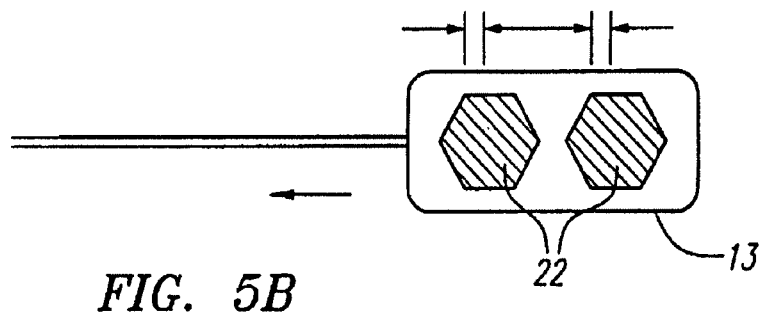

FIGS. 5A and 5B show a top view looking down through the windows 21, indicator 20 is provided with opaque portions 22. The windows 21 preferably have a shape consistent with the shape of markings 22 on the indicator 20. Thus, prior to the indicator wire 6 being axially displaced opposite of the housing 1 and/or tube 7, some or all of the windows 21 are clear, but when the indicator wire 6 is axially displaced opposite of the housing 1 and/or tube 7 as described above, markings 22 on the indicator 20 come into correspondence with the windows 21 of the indicator panel 13 as shown in FIG. 5B. When this registration occurs, trigger 8 may be pressed.

Figure 6:
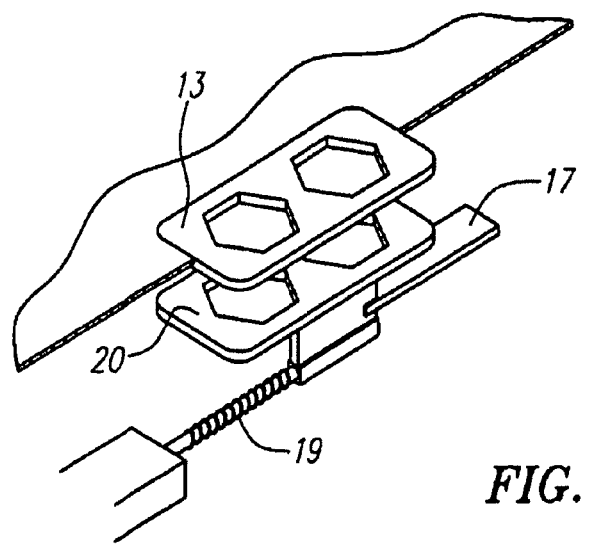
FIG. 6 illustrates a perspective view of a window portion of the sealing element deployment device in accordance with a preferred embodiment of the present invention.

FIG. 6 essentially shows the same thing as FIGS. 5A and 5B, but from a perspective view.

One of ordinary skill in the art would appreciate that though windows 21 are described, the indicator panel 21 may also utilize other mechanisms, such as electronic circuitry, light emitted diodes (LED), and/or other visual and/or audio mechanisms known in the art. For example, the device 100 may be configured such that when the indicator wire 6 engages the vessel wall 430 near the edge 415 of the tract 410, a circuit (not shown) is triggered within the housing 1 that causes a light to be emitted and/or an audio alarm to be invoked.

One of ordinary skill in the art would also appreciate that features of the anatomy of the patient's tissue can cooperate with the sealing element to facilitate the closure procedure. Preferably, the procedures of the invention position sealing element 160 so that structures located in the tissue between the patient's skin and the vessel wall 430 engage sealing element 160 and retain it against edge 415 of vessel wall 430.

For example, the transversalis fascia and the iliac fascia surround the femoral artery, forming the femoral sheath. In this region, the fasciae are relatively thick, fibrous and elastic membranes. As a result, penetration of the fasciae tend to involve a smaller puncture followed by the expansion of the hole in the fasciae to accommodate the size of the instrument forming the puncture. Upon withdrawal of the instrument, the elastic nature of the fasciae will tend to return the hole to a smaller size than the original puncture.

Figure 7:
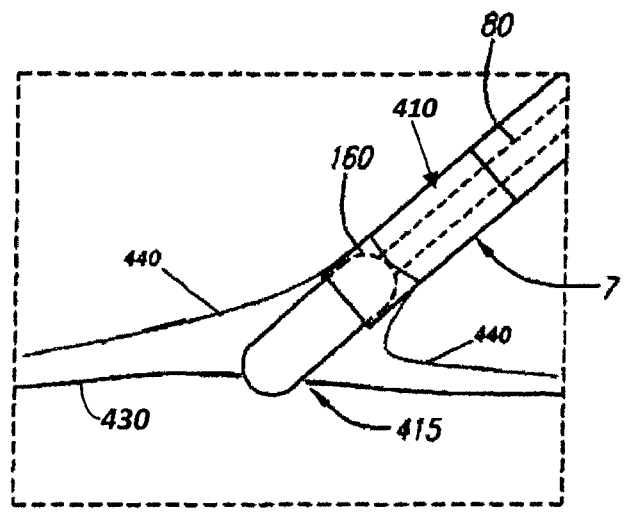
FIG. 7 illustrates a schematic view of the fascia being stretched away from the vessel wall by the deployment device in accordance with a preferred embodiment of the present invention.
Figure 8:
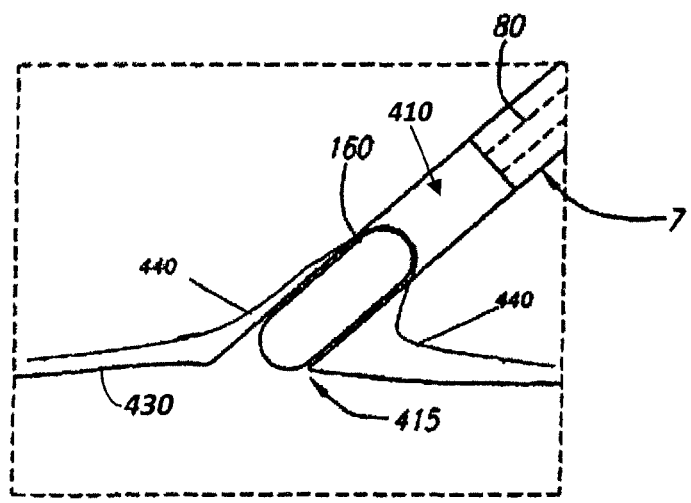
FIG. 8 illustrates a schematic view of the fascia retaining the sealing element against the vessel wall in accordance with a preferred embodiment of the present invention.
Figure 9:
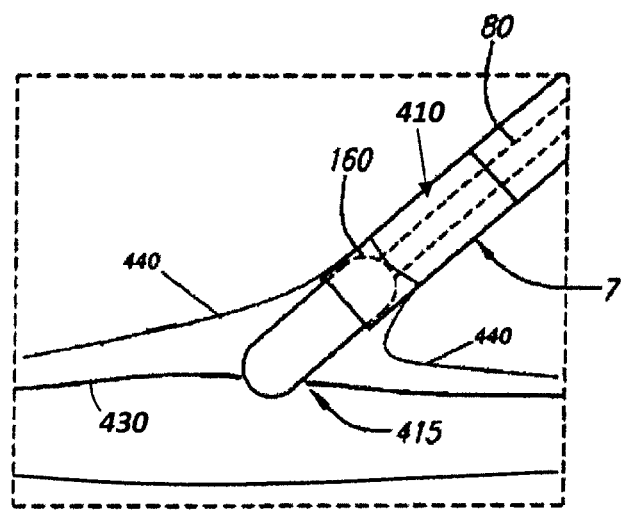
FIG. 9 illustrates another schematic view of the fascia retaining the sealing element against the vessel wall in accordance with a preferred embodiment of the present invention.

As can be seen in FIGS. 7-9, methods of the invention use these characteristics of the fasciae to help retain sealing element 150 against edge 415 of vessel wall 430. First, FIG. 7 shows an alternate detail of the operation described above with reference to FIGS. 2c and 2d. Introducer sheath 300 has been inserted through puncture wound 400, through fascia 440 and into lumen 420 of vessel 420. FIG. 7 shows the withdrawal of deployment tube 7 after sealing element 160 has been positioned adjacent edge 415 of blood vessel 430. Introducer sheath 300 has been withdrawn already, and now deployment tube 7 is being withdrawn to leave sealing element 160 in position. As shown in FIG. 7, the elastic nature of fascia 440 tends to close about deployment tube 7 so that as tube 7 is withdrawn, friction pulls fascia 440 away from vessel wall 430.

FIG. 8 shows that withdrawal of deployment tube 7 elastically displaces, or stretches, fascia 440 above sealing element 160, so that sealing element 160 is positioned between vessel wall 430 and fascia 440. When the range of travel of fascia 440 has been exceeded, fascia 440 pulls free from deployment tube and engages sealing element 160 has been placed adjacent edge 415 of vessel wall 430. Given the elastic nature of fascia 440, the size of the opening formed by introducer sheath 300 will have decreased so that the sheath cannot pass over sealing element 160. Further, the expandable nature of sealing element 160 described above will tend to prevent it from passing through an opening in the fascia 440. For example, needle-weaved PGA fibers absorb some blood volume. Accordingly, as can be seen in FIG. 8, fascia 440 forms a "tent" over sealing element 160, holding it in position adjacent edge 415. The elasticity of fascia 440 transmits force to sealing element 160 to urge it against vessel wall 430 and effectively close lumen 420.

Alternatively, FIG. 9 shows another embodiment of the invention. Here, fascia 440 has pulled free from deployment tube 7 before sealing element 160 has been completely exposed. However, fascia 440 has still been stretched away from vessel wall 430 and will constrict about sealing element 160. The resulting friction of the tissue tract and the fascia retains the sealing element 160 in position adjacent edge 415 and urges sealing element 160 against vessel wall 430. The expandable nature of sealing element 160 increases its engagement with fascia 440.

Figure 10:
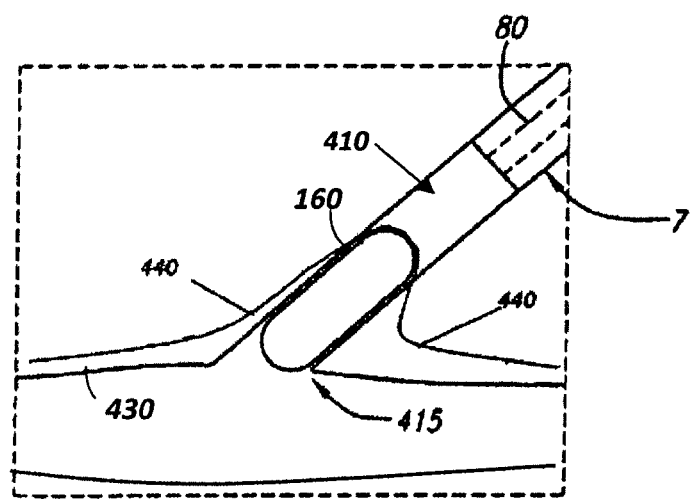
FIG. 10 illustrates another schematic view the fascia retaining the sealing element against the vessel wall in accordance with a preferred embodiment of the present invention.

FIG. 10 shows an alternative detail of the operation described above with reference to FIGS. 7 and 8. FIG. 10 shows that after the deployment tube 7 is withdrawn and the sealing element 160 is completely exposed, a portion of the sealing element 160 may be positioned in lumen 420 of vessel 430 and the remaining portion positioned within tract 410 of the wound 400. In other words, the sealing element may extend beyond edge 415 of vessel wall 430 and into the lumen 420. The fascia 440 can form a tent completely over sealing element 160 as shown in FIG. 8 or partially over sealing element 160 as shown in FIG. 9.

In addition to the interaction with the fascia 440, sealing element 160 is also stabilized and retained in position by other factors, including contraction of tissue above the tract.

Figure 11:
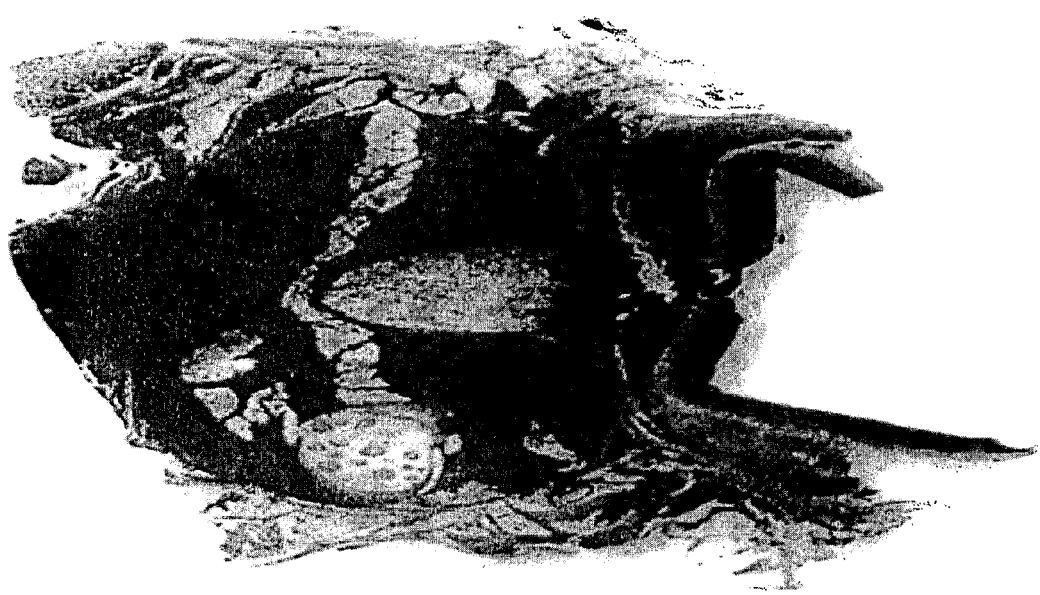
FIG. 11 is a photographic reproduction of a cross section of tissue showing the fascia retaining the sealing element against the vessel wall in accordance with a preferred embodiment of the present invention.

FIG. 11 is a photographic reproduction of a cross section of tissue showing placement of the sealing element. As can be seen, the sealing element is positioned between the fascia and the vessel wall. The elastic nature of the fascia helps retain the sealing element against the vessel wall and position it adjacent the puncture. FIG. 10 also shows that sealing element is preferably sized so that it can be positioned between the vessel wall and the fascia while maintaining the fascia in an elastically displaced position. Generally, the sealing element should be small enough to fit between the vessel wall and the elastically displaced fascia, yet large enough so that the elastically displaced fascia transmits force to the sealing element, holding it against the vessel wall.

The procedures of the invention have successfully been used to seal femoral arteriotomies. In one clinical study, average time to hemostasis using the inventive procedure averaged 138±42 sec, with patients undergoing diagnostic catheterization achieving hemostasis in 138±46 sec (45-296 sec) and patients undergoing percutaneous coronary interventions achieving hemostatis in 139±36 sec (36-245 sec) in 42 successful procedures. Notably, 83% of the patients achieved hemostasis by 2 min. Within the same study, average time to ambulation averaged 2.8 hours, with patients undergoing diagnostic catheterization ambulating in 2.78±1.23 hours (0.98-7.02 hours) and patients undergoing percutaneous coronary interventions ambulating in 2.93±1.22 hours (2.17-6.32 hours). In this study, 92% of the patients ambulated within 4 hours. The noted study experienced a 97% success rate (36/37) excluding roll-ins, where hemostasis was achieved within 5 min of plug delivery without closure-related serious adverse effects. Overall, 42 closures were achieved in 47 patients. In the study, no device-related serious adverse effects, including death, stroke, surgical repair, infection requiring hospitalization or bleeding requiring transfusion, were observed and one non-device related effect, a myocardial infarction occurred.

In the foregoing specification, the invention has been described with reference to specific embodiments thereof. It will, however, be evident that various modifications and changes may be made thereto without departing from the broader spirit and scope of the invention. For example, preferred embodiments of the invention are directed to sealing femoral arteriotomies and reference is made to the fasciae surround the femoral artery, the femoral sheath. However, the invention can be applied to other lumens and membranes in the body as desired. Further, the reader is to understand that the specific ordering and combination of process actions described herein is merely illustrative, and the invention can be performed using different or additional process actions, or a different combination or ordering of process actions. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:

1. A method for sealing a puncture, having an edge, in a wall of a lumen of a body comprising:
   a) deploying a deployment member of a sealing device through an elastic membrane adjacent an outer wall of the lumen and the puncture, wherein the sealing element is disposed within a distal portion of the deployment member and wherein the distal portion of the deployment member has a uniform diameter greater than the sealing element;
   b) positioning the sealing element adjacent the outer wall of the lumen and the edge of the puncture such that a maximal radial diameter portion of the sealing element is located outside the lumen and a reduced radial portion of the sealing element is located within the lumen;
   c) partially withdrawing the sealing element such that a portion of the reduced radial portion of the sealing element is disposed within the lumen and the remaining portion within the puncture;
   d) frictionally engaging the membrane with the deployment member;
   e) retracting the deployment member relative to the sealing element while maintaining the uniform diameter of the deployment member to stretch the membrane away from the wall of the lumen;
   f) disengaging the deployment member from the membrane wherein the membrane elastically holds the sealing member within the puncture and partially within the lumen; and
   g) retracting the device from the body to leave the maximal radial diameter portion of the sealing element outside the lumen adjacent the outer wall and the edge of the puncture.

2. The method of claim 1, wherein the elastic membrane is a fascia.

3. The method of claim 2, wherein the fascia comprises a portion of a femoral sheath.

4. The method of claim 3, wherein the lumen of the body comprises a femoral artery.

5. The method of claim 1, wherein the sealing element is positioned between the membrane and the wall of the lumen when the membrane elastically holds the sealing element.

6. The method of claim 1, wherein the sealing element partially protrudes from the membrane when the membrane elastically holds the sealing element.

7. The method of claim 1, wherein membrane retains the sealing element at a desired position adjacent the wall of the lumen.

8. The method of claim 7, wherein the membrane urges the sealing element against the wall of the lumen.

9. The method of claim 1, wherein the sealing element further includes an indicator wire having a distal tip; and further comprising the steps of extending the indicator wire out of the deployment member when the sealing element is deployed through the puncture; adjusting the position of the sealing element until the indicator wire is adjacent to the edge of the puncture; and retracting the indicator wire into the device.

* * * * *